United States Patent
Choo et al.

(10) Patent No.: US 9,194,815 B2
(45) Date of Patent: Nov. 24, 2015

(54) APPARATUS AND METHOD FOR INSPECTING CRYSTALLIZATION

(71) Applicant: SAMSUNG DISPLAY CO., LTD., Yongin, Gyeonggi-do (KR)

(72) Inventors: Byoung-Kwon Choo, Yongin (KR); Cheol-Ho Park, Yongin (KR); Hee-Geun Son, Yongin (KR); Do-Yeob Kim, Yongin (KR)

(73) Assignee: Samsung Display Co., Ltd., Yongin-si (KR)

( * ) Notice: Subject to any disclaimer, the term of this patent is extended or adjusted under 35 U.S.C. 154(b) by 255 days.

(21) Appl. No.: 13/922,075

(22) Filed: Jun. 19, 2013

(65) Prior Publication Data

US 2014/0226155 A1 Aug. 14, 2014

(30) Foreign Application Priority Data

Feb. 12, 2013 (KR) .......................... 10-2013-0014978

(51) Int. Cl.
  *G01N 21/95* (2006.01)
  *G01N 21/956* (2006.01)

(52) U.S. Cl.
  CPC .......... *G01N 21/9501* (2013.01); *G01N 21/956* (2013.01); *G01N 2021/9513* (2013.01); *G06T 2207/30148* (2013.01)

(58) Field of Classification Search
  CPC ............................................. G06T 2207/30148
  See application file for complete search history.

(56) References Cited

U.S. PATENT DOCUMENTS

| 6,136,632 | A | 10/2000 | Higashi |
| 6,541,747 | B1 * | 4/2003 | Kikuchi et al. ............ 250/201.2 |
| 6,801,650 | B1 * | 10/2004 | Kikuchi et al. ............... 382/145 |
| 6,806,099 | B2 | 10/2004 | Takeda et al. |
| 7,184,132 | B2 | 2/2007 | Tsao |
| 7,669,094 | B2 * | 2/2010 | Dembo ......................... 714/718 |
| 8,404,498 | B2 * | 3/2013 | Amago et al. .................. 438/16 |
| 2003/0113007 | A1 * | 6/2003 | Iwasaki et al. ................ 382/141 |
| 2005/0246128 | A1 * | 11/2005 | Urisu ............................ 702/120 |
| 2006/0221333 | A1 * | 10/2006 | Matsumoto ................ 356/239.7 |
| 2009/0222135 | A1 * | 9/2009 | Asakawa et al. .............. 700/253 |
| 2010/0017015 | A1 * | 1/2010 | Morii ............................ 700/213 |
| 2011/0080998 | A1 * | 4/2011 | Saito et al. ...................... 378/50 |
| 2011/0096158 | A1 * | 4/2011 | Nagai ............................. 348/95 |

FOREIGN PATENT DOCUMENTS

| JP | 2003-109902 | 4/2003 |
| KR | 10-2005-0004081 | 1/2005 |
| KR | 10-2012-0035860 | 4/2012 |
| KR | 10-2012-0060162 A | 6/2012 |
| WO | WO97/23806 | 7/1997 |

* cited by examiner

*Primary Examiner* — Utpal Shah
(74) *Attorney, Agent, or Firm* — Christie, Parker & Hale, LLP (57) ABSTRACT

An apparatus for inspecting crystallization includes a substrate including a semiconductor layer, the semiconductor layer includes a plurality of crystallized regions separated from each other; a stage configured to change a position of the substrate, the substrate being seated thereon; a photographing unit configured to acquire image data regarding the semiconductor layer; an inspection unit configured to obtain inspection data regarding the semiconductor layer; and a control unit configured to output change data regarding a change in the position of the substrate according to the image data acquired by the photographing unit.

9 Claims, 7 Drawing Sheets

APPARATUS AND METHOD FOR INSPECTING CRYSTALLIZATION

CROSS-REFERENCE TO RELATED PATENT APPLICATION

This application claims priority to and the benefit of Korean Patent Application No. 10-2013-0014978, filed on Feb. 12, 2013 in the Korean Intellectual Property Office, the disclosure of which is incorporated herein in its entirety by reference.

BACKGROUND

1. Field

The following description relates to an apparatus and method for inspecting crystallization.

2. Description of the Related Art

Organic light-emitting display or liquid crystal display apparatuses generally use thin-film transistors (TFTs) to control the light emission or intensity of light emission from each pixel. A TFT includes a semiconductor layer, a gate electrode, and source/drain electrodes. The semiconductor layer may be typically formed of polysilicon formed by crystallizing amorphous silicon.

A conventional method of fabricating a display device using a TFT substrate having TFTs formed thereon includes forming an amorphous silicon layer over a substrate and crystallizing the amorphous silicon layer into a polysilicon layer.

However, the conventional method is complicated and requires significant cost and/or time to crystallize the amorphous silicon layer into the polysilicon layer and to then inspect the crystallization. Thus, it is desirable to provide apparatuses and methods to reduce the cost and/or time involved.

SUMMARY

Aspects of embodiments of the present invention are directed toward an apparatus and method for inspecting crystallization which allows automatic inspection of a crystallized semiconductor layer.

According to an embodiment of the present invention, there is provided an apparatus for inspecting crystallization including: a stage configured to change a position of a substrate, the substrate being seated thereon and including a semiconductor layer, the semiconductor layer including a plurality of crystallized regions separated from each other; a photographing unit configured to acquire image data regarding the semiconductor layer; an inspection unit configured to obtain inspection data regarding the semiconductor layer; and a control unit configured to output change data regarding a change in the position of the substrate according to the image data acquired by the photographing unit.

The control unit may be further configured to output the change data according to brightness data in the image data.

The control unit may be further configured to output the change data such that the inspection unit can obtain inspection data regarding at least one of the plurality of crystallized separate regions.

The control unit may be further configured to determine that one of the plurality of crystallized separate regions is a portion of the semiconductor layer having a brightness in a second brightness range and located between other portions of the semiconductor layer having brightnesses in a first brightness range, wherein the second brightness range includes values that are greater than those of the first brightness range.

The control unit may be further configured to determine that one of the plurality of crystallized separate regions is a portion of the semiconductor layer having a brightness between peak brightnesses and in a preset brightness range.

A position of the photographing unit may be fixed relative to a position of the inspection unit.

According to another embodiment of the present invention, there is provided an apparatus for inspecting crystallization including: a substrate seating portion on which a substrate is seated, the substrate including a semiconductor layer, the semiconductor layer including a plurality of crystallized regions separated from each other; a photographing unit configured to acquire image data regarding the semiconductor layer; an inspection unit configured to obtain inspection data regarding the semiconductor layer; a position changing unit configured to change positions of the photographing unit and the inspection unit with respect to the substrate seating portion; and a control unit configured to output change data regarding a change in the positions of the photographing unit and the inspection unit according to the image data acquired by the photographing unit.

The control unit may be further configured to output the change data according to brightness data in the image data.

The control unit may be further configured to output the change data such that the inspection unit can obtain inspection data regarding at least one of the plurality of crystallized separate regions.

The control unit may be further configured to determine that one of the plurality of crystallized separate regions is a portion of the semiconductor layer having a brightness in a second brightness range and located between other portions of the semiconductor layer having brightnesses in a first brightness range, wherein the second brightness range includes values that are greater than those of the first brightness range.

The control unit may be further configured to determine that one of the plurality of crystallized separate regions is a portion of the semiconductor layer having a brightness between peak brightnesses and in a preset brightness range.

A position of the photographing unit may be fixed relative to a position of the inspection unit.

According to another embodiment of the present invention, there is provided an apparatus for inspecting crystallization including: a stage configured to change a position of a substrate, the substrate being seated thereon and including a semiconductor layer including a plurality of crystallized regions separated from each other by an interval; a photographing unit configured to acquire image data regarding positions of markers on the substrate; an inspection unit configured to obtain inspection data regarding the semiconductor layer; and a control unit configured to output change data regarding a change in the position of the substrate such that the position of the substrate is repeatedly changed by the interval.

The control unit may be further configured to output initial change data such that the position of the substrate with respect to the inspection unit is at a set position according to the image data.

When the substrate is at the set position, the inspection unit may obtain inspection data regarding at least one of the plurality of crystallized separate regions.

A position of the photographing unit may be fixed relative to a position of the inspection unit.

According to another embodiment of the present invention, there is provided an apparatus for inspecting crystallization including: a substrate seating portion on which a substrate is seated, the substrate including a semiconductor layer including a plurality of crystallized regions separated from each other by an interval; a photographing unit configured to acquire image data regarding markers on the substrate; an inspection unit configured to obtain inspection data regarding the semiconductor layer; a position changing unit configured to change a position of the inspection unit with respect to the substrate seating portion; and a control unit configured to output change data regarding a change in the position of the inspection unit such that the position of the inspection unit is repeatedly changed by the interval.

The control unit may be further configured to output initial change data such that the position of the inspection unit with respect to the substrate is at a set position according to the image data.

When the inspection unit is at the set position, the inspection unit may obtain inspection data regarding at least one of the plurality of crystallized separate regions.

A position of the photographing unit may be fixed relative to the position of the inspection.

According to another embodiment of the present invention, there is provided a method of inspecting crystallization including: preparing a substrate including a semiconductor layer including a plurality of crystallized regions separated from each other; changing at least one position of the substrate or an inspection unit according to image data acquired regarding the semiconductor layer to obtain inspection data regarding at least one of the plurality of crystallized separate regions; obtaining the inspection data regarding the at least one of the plurality of crystallized separate regions; changing the at least one position of the substrate or the inspection unit according to the image data acquired regarding the semiconductor layer to obtain inspection data regarding another one of the plurality of crystallized separate regions; and obtaining the inspection data regarding the another one of the plurality of crystallized separate regions.

The at least one position of the substrate or the inspection unit may be changed according to brightness data in the acquired image data.

The at least one position of the substrate or the inspection unit may be changed by determining that one of the plurality of crystallized separate regions is a portion of the semiconductor layer having a brightness in a second brightness range and located between other portions of the semiconductor layer having brightnesses in a first brightness range, wherein the second brightness range includes values that are greater than those of the first brightness range.

The at least one position of the substrate or the inspection unit may be changed by determining that one of the plurality of crystallized separate regions is a portion of the semiconductor layer having a brightness between peak brightnesses and in a brightness range.

The changing of the at least one position of the substrate or the inspection unit to obtain inspection data regarding the another one of the plurality of crystallized separate regions and the obtaining of the inspection data regarding the another one of the plurality of crystallized separate regions may be repeated.

According to another embodiment of the present invention, there is provided a method of inspecting crystallization including: preparing a substrate including a semiconductor layer including a plurality of crystallized regions separated from each other by an interval; changing at least one position of the substrate or an inspection unit according to image data acquired regarding markers on the substrate to obtain inspection data regarding at least one of the plurality of crystallized separate regions; obtaining the inspection data regarding the at least one of the plurality of crystallized separate regions; changing the at least one position of the substrate or the inspection unit by the interval to obtain inspection data regarding another one of the plurality of crystallized separate regions; and obtaining the inspection data for the another one of the plurality of crystallized separate regions.

The changing of the at least one position of the substrate or the inspection unit to obtain inspection data regarding the another one of the plurality of crystallized separate regions and the obtaining of the inspection data regarding the another one of the plurality of crystallized separate regions may be repeated.

The apparatus and method for inspecting crystallization allows automatic inspection of a crystallized semiconductor layer. However, the scope of the present invention is not limited by these effects and aspects.

BRIEF DESCRIPTION OF THE DRAWINGS

The above and other features and aspects of the present invention will become more apparent by describing, in detail, example embodiments thereof with reference to the attached drawings in which.

DETAILED DESCRIPTION

Example embodiments of the invention will now be described more fully hereinafter with reference to the accompanying drawings, in which example embodiments of the invention are shown. The example embodiments are provided so that this disclosure will be thorough and complete and will fully convey the scope of the invention to those skilled in the art. This invention may, however, be embodied in many different forms and should not be construed as limited to the example embodiments set forth herein. For convenience of explanation, sizes of layers, regions, and/or other elements may be exaggerated or reduced for clarity. For example, the size and thickness of each element may not be limited to those illustrated in the drawings.

In the example embodiments below, x, y, and z axes are not limited to three axes in an orthogonal coordinate system but can be constructed to include any three suitable axes. For example, x, y, and z axes may not be orthogonal to each other and represent three different directions that are not orthogonal to each other.

It will be understood that when an element such as a layer, film, region, or substrate is referred to as being "on" or "over" another element, it can be directly on the other element or intervening element(s) may also be present.

As used herein, the term "and/or" includes any and all combinations of one or more of the associated listed items. Expressions such as "at least one of," when preceding a list of elements, modify the entire list of elements and do not modify the individual elements of the list.

Figure 1:
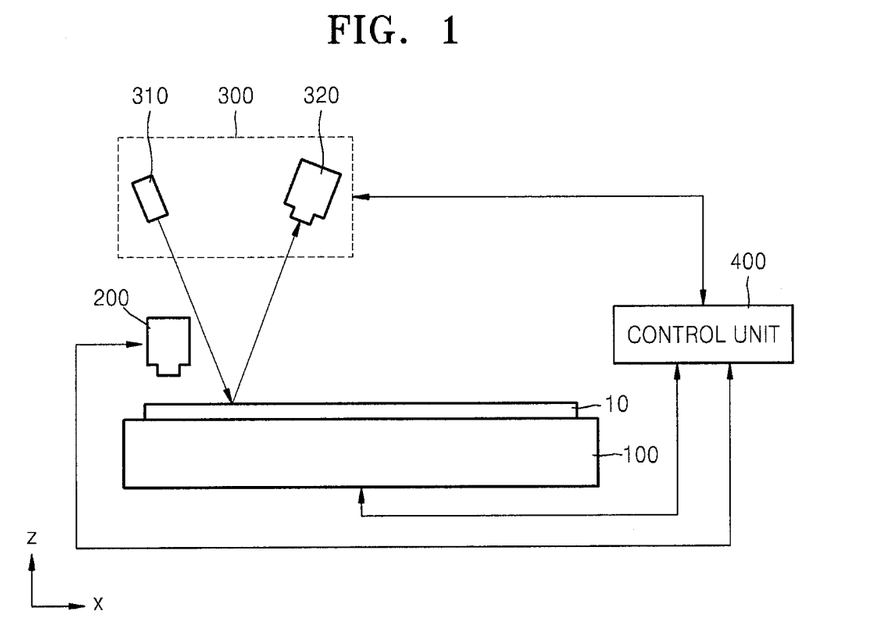
FIG. 1 is a conceptual side diagram schematically illustrating an apparatus for inspecting crystallization, according to an embodiment of the present invention.

FIG. 1 is a conceptual side diagram schematically illustrating an apparatus for inspecting crystallization according to an embodiment of the present invention. Referring to FIG. 1, the apparatus for inspecting crystallization, according to the present embodiment, includes a stage 100 on which a substrate 10 is seated, a photographing unit 200, an inspection unit 300, and a control unit 400.

A position of the substrate 10 may vary, for example, on an x-y plane. The substrate 10 has a silicon layer on a top surface thereof (e.g., a surface in the +z direction). The silicon layer may be formed on the entire top surface of the substrate 10 or most of the top surface thereof so as not to cover a portion of the top surface, such as edges thereof.

The substrate 10 may be loaded onto the stage 100 by using various suitable methods. For example, when a plurality of pins that are movable up and down (e.g., in the z-axis direction) are raised to project up from the top surface (e.g., in the +z direction) of the stage 100 through a plurality of through holes that pass through the stage 100, the substrate 10 may be placed on the plurality of pins by a robot (e.g., a transport robot), and the plurality of pins may then be lowered (e.g., in the −z direction) to seat and support the substrate 10 on the stage 100.

Although not shown in FIG. 1, the substrate 10 has a silicon layer (e.g., a semiconductor layer) formed thereon. The semiconductor layer includes a plurality of crystallized regions separated from each other and a remaining uncrystallized region. For example, an amorphous silicon layer may be formed on the substrate 10, with only a portion (e.g., a preset portion) thereof being crystallized (e.g., selectively crystallized).

The amorphous silicon layer may be crystallized by using various suitable methods. For example, the amorphous silicon layer may be irradiated with a laser beam for crystallization. The laser beam is typically a spot beam or line beam. Thus, it may take a long time to irradiate a laser beam on the entire surface of the amorphous silicon layer because a region of the amorphous silicon layer to be irradiated has to be changed many times.

One approach to reducing the time required to crystallize the amorphous silicon layer is to irradiate a laser beam only on regions (e.g., set or predetermined regions) corresponding to a portion of a silicon layer on which a TFT will be located instead of irradiating the entire surface of the silicon layer. This approach may significantly reduce the time needed to crystallize the silicon layer. However, this approach is inefficient in the absence of an apparatus or method for automatically inspecting the silicon layer in which only the separate regions (e.g., set separate regions) have been crystallized.

Because a silicon layer having the entire surface thereof crystallized has uniform characteristics across the whole surface thereof, it is possible to automatically inspect the silicon layer by scanning its entire surface. Conversely, for a silicon layer with crystallized separate regions and a remaining amorphous region, automatic inspection cannot be performed on the silicon layer (e.g., on the entire silicon layer) due to the occurrence of noise in (e.g., created by) the amorphous region. Thus, the apparatus for inspecting crystallization, according to embodiments of the present invention, or a method for inspecting crystallization, according to embodiments of the present invention, as described below may be used to solve this noise problem and/or to automatically inspect the silicon layer with crystallized separate regions.

The photographing unit 200 acquires image data regarding the semiconductor layer on the substrate 10 seated on the stage 100. To accomplish this, the photographing unit 200 may include an imaging device such as a charge-coupled device (CCD) or complementary metal-oxide-semiconductor (CMOS) imaging device. The photographing unit 200 may be located (e.g., disposed) at various locations. For example, as illustrated in FIG. 1, the photographing unit 200 may be disposed above (e.g., in the +z direction) the stage 100.

The inspection unit 300 acquires inspection data regarding the semiconductor layer on the substrate 10. The inspection unit 300 may be formed using various elements and configurations. For example, the inspection unit 300 may be a reflective inspection unit as shown in FIG. 1 and include a light source 310 for emitting light of a set or predetermined wavelength and an inspection data acquirer 320 for acquiring data from the light emitted by the light source 310 and reflected from the silicon layer on the substrate 10. The inspection data acquirer 320 may have a similar configuration to the photographing unit 200, such as including an imaging device such as a CCD or a CMOS imaging device. The inspection unit 300 may use light of a specific wavelength to obtain data with enhanced contrast of light interference fringes due to a change in a thickness of the silicon layer. Thus, the resolution of inspection data acquired regarding the semiconductor layer may be increased.

The inspection unit 300 is not limited to the reflective inspection unit and may be various suitable inspection units, such as a transmissive inspection unit in which light emitted by a high brightness, white LED light source passes through the substrate 10 and inspection data regarding the semiconductor layer is obtained by using a brightness difference between the transmitted and received light.

The control unit 400 outputs change data regarding a change in a position of the substrate 10 seated on the stage 100 based on the image data acquired by the photographing unit 200.

In the apparatus for inspecting crystallization according to a present embodiment, because the semiconductor layer on the substrate 10 has crystallized separate regions and a remaining amorphous region instead of having an entirely crystallized surface, the control unit 400 outputs change data regarding a change in a position of the substrate 10 based on image data obtained by the photographing unit 200, and the stage 100 adjusts a position of the substrate 10 according to the change data outputted from the control unit 400. Thus, inspection data can be obtained for (e.g., related to) only the crystallized regions of the semiconductor layer. In other words, because inspection data is not obtained for the remaining amorphous region (e.g., the uncrystallized region), the occurrence of noise may be reduced or prevented.

Furthermore, the inspection unit 300 inspects only the crystallized regions of the semiconductor layer based on (e.g., according to) the image data obtained by the photographing unit 200, thereby allowing faster, automated inspection.

A process of detecting the crystallized regions of the semiconductor layer to be inspected based on image data obtained by the photographing unit 200 is hereinafter described in more detail.

Figure 2:
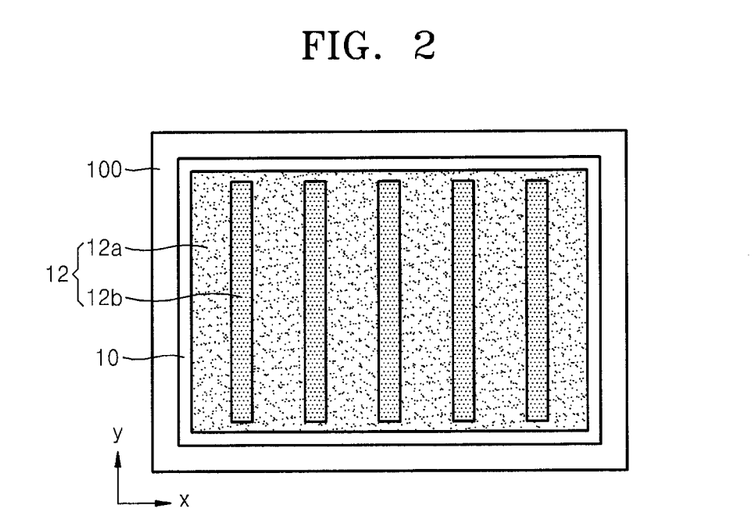
FIG. 2 is a schematic plan view of a substrate and a semiconductor layer to be inspected.

FIG. 2 is a schematic plan view of the substrate 10 with a semiconductor layer 12 to be inspected. Referring to FIG. 2, the semiconductor layer 12 is formed on the substrate 10 that rests on the stage 100. The semiconductor layer 12 includes a plurality of crystallized separate regions 12b and a remaining uncrystallized region 12a.

Figure 3:
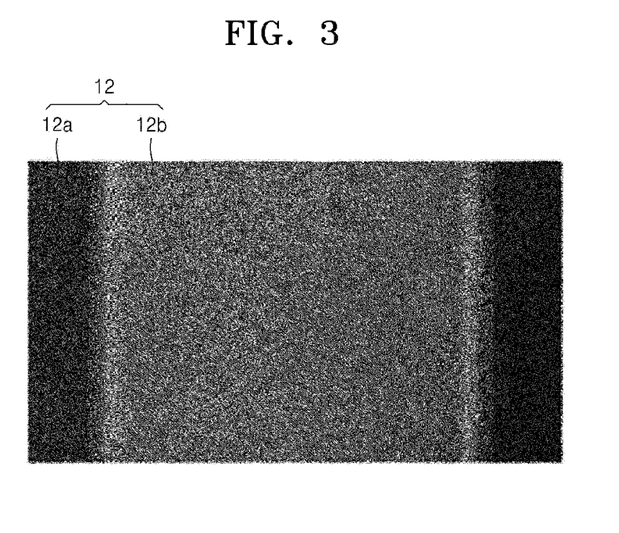
FIG. 3 is a photograph showing a to-be-inspected portion of the semiconductor layer on a substrate.

FIG. 3 is a photograph showing a to-be-inspected portion of a semiconductor layer 12 on a substrate.

Figure 4:
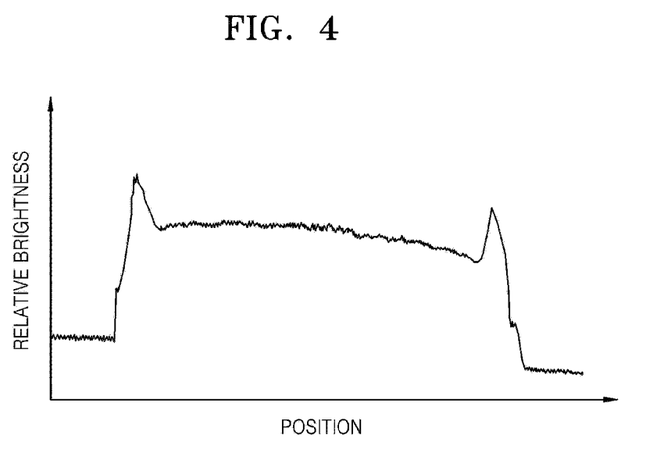
FIG. 4 is a graph of relative brightness with respect to a position on the semiconductor layer shown in FIG. 3.

As shown in FIG. 3, a crystallized region 12b and a remaining region 12a in the semiconductor layer 12 have different brightnesses. More specifically, the crystallized region 12b has a brightness that is greater than a brightness of the remaining region 12a, which is an uncrystallized amorphous silicon region. FIG. 4 is a graph of relative brightness with respect to a position on the semiconductor layer 12 (e.g., a region of the semiconductor layer 12) corresponding to FIG. 3. The change in brightness as illustrated in FIG. 3 can also be seen from the graph in FIG. 4, which is a visual representation of numerical data.

The control unit 400 uses brightness data in (e.g., contained in) the image data obtained by the photographing unit 200 to output change data regarding a change in a position of the substrate 10. In other words, the control unit 400 may output the change data by using the brightness data so that the inspection unit 300 acquires inspection data regarding at least one of (e.g., some of) the plurality of separate crystallized regions 12b in the semiconductor layer 12.

Figure 5:
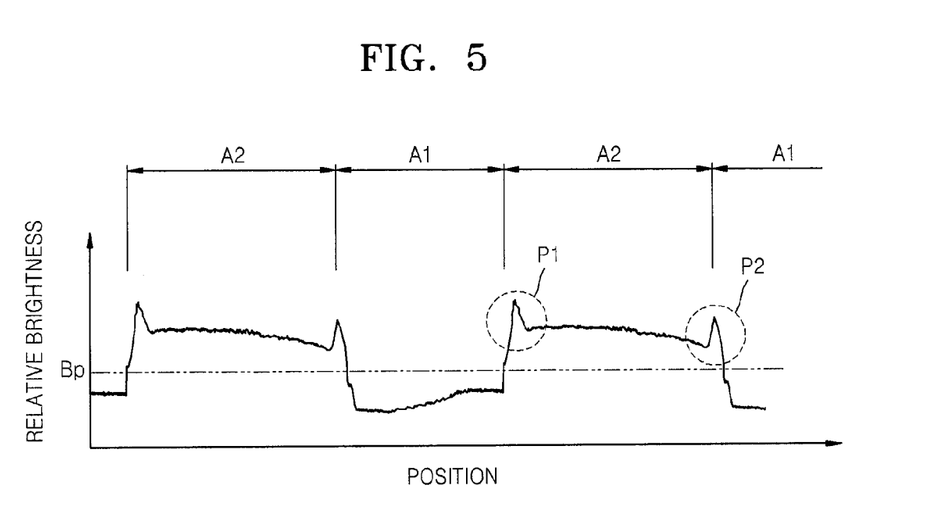
FIG. 5 is a graph of relative brightness with respect to a position on a semiconductor layer.

FIG. 5 is a graph of relative brightness with respect to a position on the semiconductor layer 12. The control unit 400 may determine that a portion A2 of the semiconductor layer 12, having a brightness in a second brightness range and being between the remaining portions A1 having brightnesses in a first brightness range, belongs to the plurality of crystallized separate regions 12b (e.g., is one of the plurality of crystallized separate regions 12b), wherein the second brightness range includes values that are greater than those of the first brightness range. Alternatively, the control unit 400 may determine that the portion A2, having a brightness that is greater than a brightness level Bp (e.g., a preset brightness level Bp), belongs to (e.g., is one of) the plurality of crystallized separate regions 12b.

As described above, the control unit 400 determines positions of the plurality of crystallized separate regions 12b using the brightness data obtained by the photographing unit 200 and outputs change data regarding a change in a position of the substrate 10 resting on the stage 100 so as to acquire inspection data from the plurality of crystallized separate regions 12b. The stage 100 changes the position of the substrate 10 according to the received change data so that an inspection may be automatically conducted on (e.g., only on) the plurality of crystallized separate regions 12b in the semiconductor layer 12. To achieve this, the position of the photographing unit 200 may be fixed relative to the position of the inspection unit 300.

The control unit 400 may determine the positions of the plurality of crystallized separate regions 12b from the data acquired by the photographing unit 200 by using a different method than described above. Referring to FIGS. 3 through 5, a peak brightness appears at boundaries between each of the plurality of crystallized separate regions 12b and the remaining uncrystallized region 12a. In other words, although the crystallized portions A2 have brightnesses greater than those of the uncrystallized portions A1, peak brightnesses P1 and P2 (e.g., brightnesses greater than those of crystallized portions A2) occur at each boundary between the crystallized and uncrystallized portions A1 and A2 of the semiconductor layer 12.

By using these characteristics, the control unit 400 may determine that of the portions A1 and A2 of the semiconductor layer 12 on the substrate 10 which are located between other portions of the semiconductor layer having the peak brightnesses P1 and P2, the portion A2 having a brightness within a brightness range (e.g., a set or predetermined brightness range) greater than a brightness Bp (e.g., a preset brightness Bp) belongs to (e.g., is one of) the plurality of crystallized separate regions 12b.

Figure 6:
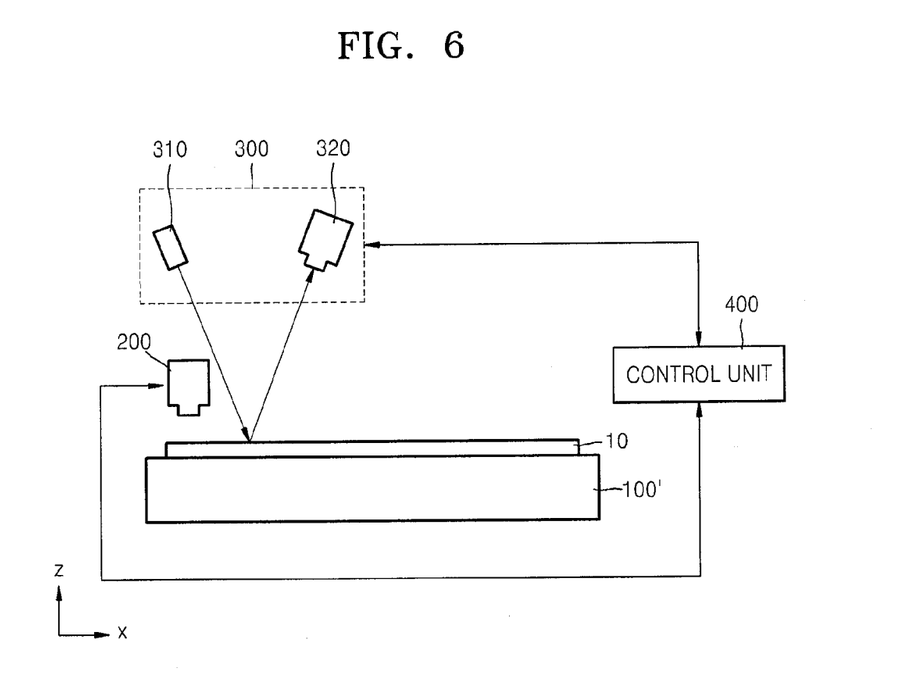
FIG. 6 is a conceptual side diagram schematically illustrating an apparatus for inspecting crystallization, according to another embodiment of the present invention.

FIG. 6 is a conceptual side diagram schematically illustrating an apparatus for inspecting crystallization according to another embodiment of the present invention. A difference from the apparatus described with reference to FIG. 1 is that the apparatus according to the present embodiment further includes a position changing unit which changes positions of the photographing unit 200 and the inspection unit 300 with respect to a substrate seating portion 100'. Another difference is that the apparatus according to the present embodiment includes the substrate seating portion 100' on which a substrate 10 is fixedly seated, instead of the stage (100 in FIG. 1) that can change a position of the substrate 10 resting thereon. Thus, in the apparatus for inspecting crystallization according to the present embodiment, the position of the substrate 10 remains unchanged during inspection.

The apparatus for inspecting crystallization according to the present embodiment includes the photographing unit 200 which acquires image data regarding a semiconductor layer on the substrate 10 seated on the substrate seating portion 100', the inspection unit 300 which obtains inspection data regarding the semiconductor layer on the substrate 10, and the control unit 400 which outputs change data regarding a change in positions of the photographing unit 200 and the inspection unit 300 based on the image data acquired by the photographing unit 200. The position changing unit changes the positions of the photographing unit 200 and the inspection unit 300 with respect to the substrate seating portion 100' according to the change data, and the inspection unit 300 may then obtain inspection data regarding a plurality of crystallized separate regions 12b in the semiconductor layer 12 on the substrate 10. To achieve this, the position of the photographing unit 200 may be fixed relative to the position of the inspection unit 300 or vice versa.

According to the present embodiment, a position of the substrate 10 is maintained when the substrate 10 rests on the substrate seating portion 100' during inspection. As such, the positions of the photographing unit 200 and the inspection unit 300 with respect to the substrate sealing portion 100' are changed by the position changing unit to conduct inspection on or of the semiconductor layer 12 on the substrate 10. Thus, the overall size of the apparatus may be significantly reduced because the apparatus does not require a space available to move the substrate 10, requiring a wide area, during the inspection. The position changing unit changes the positions of the photographing unit 200 and the inspection unit 300 after receiving the change data output from the control unit 400.

The change data regarding a change in position outputted from the control unit 400 may be generated in substantially the same manner as described above with reference to FIGS. 1 through 5.

The control unit 400 uses brightness data in the image data obtained by the photographing unit 200 to output change data regarding a change in positions of the photographing unit 200 and the inspection unit 300. More specifically, when the position changing unit changes the positions of the photographing unit 200 and the inspection unit 300, the control unit 400 may output change data so that the inspection unit 300 acquires inspection data regarding at least one of (e.g., some of) the plurality of separate crystallized regions 12b in the semiconductor layer 12 according to the position change.

In order to generate and output the change data, as shown in FIG. 5, the control unit 400 may determine that the portion A2 of the semiconductor layer 12, having a brightness in a second brightness range and between the portions A1 having brightnesses in a first brightness range, belongs to (e.g., is one of) the plurality of crystallized separate regions 12b, wherein the second brightness range is greater than the first brightness range (e.g., the second brightness range includes values that are greater than those of the first brightness range). Alternatively, the control unit 400 may determine that a portion of the semiconductor layer 12 having a brightness in a brightness range (e.g., a set or predetermined brightness range) and located between portions of the semiconductor layer having the peak brightnesses P1 and P2 belongs to (e.g., is one of) the plurality of crystallized separate regions 12b. For example, referring to FIG. 5, the control unit 400 may determine that of the portions. A1 and A2 of the semiconductor layer 12 located between other portions of the semiconductor layer having the peak brightnesses P1 and P2, the portion A2 having a brightness within a brightness range (e.g., a set or predetermined brightness range) greater than the brightness Bp (e.g., the set brightness Bp) belongs to (e.g., is one of) the plurality of crystallized separate regions 12b.

While it is described above that the photographing unit 200 is located (e.g., disposed) above the stage 100 or the substrate seating portion 100' so as to observe a top surface of the substrate 10, which rests on the stage 100 or the substrate seating portion 100', the present invention is not limited thereto.

Figure 7:
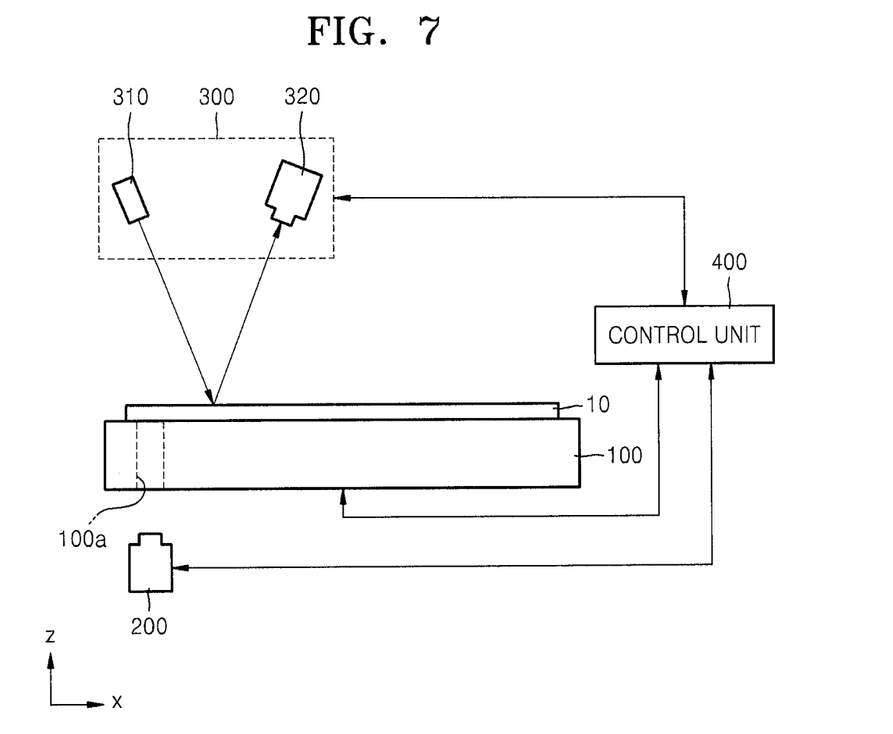
FIG. 7 is a conceptual side diagram schematically illustrating an apparatus for inspecting crystallization, according to another embodiment of the present invention.

FIG. 7 is a conceptual side diagram schematically illustrating an apparatus for inspecting crystallization, according to another embodiment of the present invention. Referring to FIG. 7, a photographing unit 200 may be located below a stage 100 (e.g., opposite [−z direction] to a direction [+z direction] in which a substrate 10 is loaded onto the stage 100). In this case, a through hole 100a corresponding to or for the photographing unit 200 is formed in the stage 100 so that the photographing unit 200 can acquire image data regarding at least a portion of a semiconductor layer on the substrate 10 supported by the stage 100. Furthermore, when the substrate 10 is made of glass or light-transmissive plastic material, the photographing unit 200 may obtain image data regarding at least a portion of the semiconductor layer 12 on the substrate 10.

The apparatus according to the present embodiment may have a similar configuration to, but perform different operations than, the apparatus described above with reference to FIG. 1.

Figure 8:
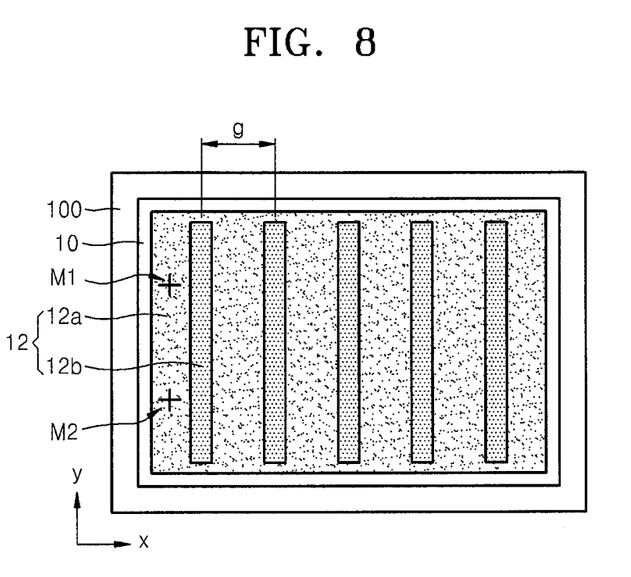
FIG. 8 is a schematic plan view of a substrate and a semiconductor layer to be inspected.

FIG. 8 is a schematic plan view of a substrate 10 and a semiconductor layer 12 to be inspected. For example, as shown in FIG. 8, the substrate 10 seated on the stage 100 may have markers M1 and M2 formed thereon. The markers M1 and M2 may be formed at or on a portion of the substrate 10 that is covered with the semiconductor layer 12 or at outer edges thereof that are not covered with the semiconductor layer 12.

The markers M1 and M2 may be formed prior to formation of the semiconductor layer 12 including amorphous silicon on the substrate 10. Alternatively, the markers M1 and M2 may be created after formation of the semiconductor layer 12 on the substrate 10 but before irradiation of a laser beam for crystallization on a region (e.g., a set region) of the semiconductor layer 12. In this case, the markers M1 and M2 may be formed or created by a marker forming element in a laser annealing apparatus.

After forming the semiconductor layer 12 on the substrate 10 on which the markers M1 and M2 have been created, a region (e.g., a set region) of the semiconductor layer 12 may be irradiated with a laser beam for crystallization. In this case, a plurality of regions which are separated from each other at intervals (e.g., at regular intervals) may be irradiated with the laser beam, using the markers M1 and M2 as reference positions, so that the semiconductor layer 12 overlying the substrate 10 may have a plurality of crystallized separate regions 12b formed therein.

The substrate 10 having the semiconductor layer 12 formed thereon including the crystallized regions 12b formed by the above process and other uncrystallized regions 12a may be seated on the stage 100. The photographing unit 200 may acquire image data regarding the markers M1 and M2 on the substrate 10. The image data may provide information about the positions of the markers M1 and M2 relative to the photographing unit 200. The control unit 400 uses the image data acquired by the photographing unit 200 to output initial change data so that a position of the substrate 10 with respect to the inspection unit 300 is at a position (e.g., a set position).

The initial change data may be construed as data specifying a distance by which the stage 100 moves the substrate 10 so that the inspection unit 300 acquires inspection data regarding at least one of (e.g., some of) the plurality of crystallized separate regions 12b in the semiconductor layer 12. Such initial change data may be determined by using positions of the markers M1 and M2 relative to the photographing unit 200.

Upon seating the substrate 10 on the stage 100, the positions of the markers M1 and M2 relative to the photographing unit 200 may not always be constant. In this case, a region of the semiconductor layer 12 on the substrate 10 to be inspected by the inspection unit 300 may be a crystallized region or not. Thus, after determining the positions of the markers M1 and M2 relative to the photographing unit 200 from (e.g., using) the image data acquired by the photographing unit 200, the control unit 400 may output initial change data to control the stage 100 to change a position of the substrate 10 according to the initial change data so that the markers M1 and M2 are located at positions (e.g., at preset positions) relative to the photographing unit 200 (e.g., the inspection unit 300 can acquire inspection data regarding at least one of the plurality of crystallized separate regions 12b).

After the substrate 10 is located or positioned so that the inspection unit 300 acquires inspection data regarding at least one of (e.g., some of) the plurality of crystallized separate regions 12b in the semiconductor layer 12 on the substrate 10 resting on the stage 100, a subsequent inspection may be conducted on the other ones of the plurality of crystallized separate regions 12b without needing to use the photographing unit 200.

More specifically, because the plurality of crystallized separate regions 12b are arranged at intervals (e.g., predetermined intervals) on the semiconductor layer 12 on or overlying the substrate 10, the stage 100 may move the substrate 10 by the corresponding interval (e.g., the predetermined interval) (e.g., in the −x direction) so that the inspection unit 300 acquires inspection data only regarding the plurality of crystallized separate regions 12b in the semiconductor layer 12. In this case, the control unit 400 may output change data regarding a change in the position of the substrate 10 so as to repeatedly alter the position of the substrate 10 by the corresponding interval (e.g., the predetermined interval). To achieve this, the position of the photographing unit 200 may be fixed relative to the position of the inspection unit 300.

When the semiconductor layer 10 has a plurality of crystallized regions separated from each other at intervals (e.g., predetermined intervals), even in the absence of the markers M1 and M2, the control unit 400 may use brightness data acquired by the photographing unit 200 to identify a position of one of the plurality of crystallized separate regions 12b so that the inspection unit 300 obtains inspection data regarding the corresponding crystallized region 12b. Thereafter, the stage 100 may repeatedly move the substrate 10 by the corresponding interval (e.g., the predetermined interval) so that the inspection unit 300 acquires inspection data regarding the remaining ones of the plurality of crystallized separate regions 12b.

While the apparatus according to the embodiment described above with reference to FIG. 8 includes the stage 100, the present invention is not limited thereto. For example, an apparatus for inspecting crystallization according to another embodiment may have a substantially similar configuration as that described with reference to FIG. 6. Specifically, the apparatus according to the present embodiment may further include a position changing unit for changing positions of a photographing unit 200 and an inspection unit 300 with respect to a substrate seating portion 100', and may include the substrate seating portion 100' on which the substrate 10 fixedly rests instead of the stage 100 that can change a position of the substrate 10 seated thereon. In other words, the apparatus according to the present embodiment may maintain the position of the substrate 10 during inspection.

In the apparatus according to the present embodiment, the photographing unit 200 acquires image data of markers M1 and M2 on the substrate 10 seated on the substrate seating portion 100'. The image data may provide information about the positions of the markers M1 and M2 relative to the photographing unit 200. A control unit 400 uses the image data acquired by the photographing unit 200 to output initial change data so that the inspection unit 300 is located (e.g., moves to be located) at a position (e.g., a set position) relative to the substrate 10 resting on the substrate seating portion 100'.

The initial change data may be construed as data specifying a distance by which the position changing unit moves the inspection unit 300 so that the inspection unit 300 acquires inspection data regarding at least one of (e.g., some of) a plurality of crystallized regions 12b in a semiconductor layer 12 separated from each other at or by intervals (e.g., predetermined intervals). Such initial change data may be determined by using positions of the markers M1 and M2 relative to the photographing unit 200.

As long as the substrate 10 is located or positioned so that the inspection unit 300 acquires inspection data regarding at least one of (e.g., some of) the plurality of crystallized separate regions 12b in the semiconductor layer 12 on the substrate 10 resting on the substrate seating portion 100', a subsequent inspection may be conducted on other ones of the plurality of crystallized separate regions 12b without needing to use the photographing unit 200. More specifically, because the plurality of crystallized separate regions 12b are arranged at intervals (e.g., predetermined intervals) on the semiconductor layer 12 overlying the substrate 10, the position changing unit may subsequently move the inspection unit 300 relative to the substrate 10 by a corresponding interval (e.g., the predetermined interval) (e.g., in the +x direction) so that the inspection unit 300 acquires inspection data regarding the other ones of the plurality of crystallized separate regions 12b in the semiconductor layer 12. In this case, the control unit 400 may output change data regarding a change in the position of the inspection unit 300 so as to repeatedly alter the position of the inspection unit 300 according to the corresponding intervals (e.g., the predetermined intervals).

In the apparatus according to the present embodiment, the position of the photographing unit 200 relative to the position of the inspection unit 300 may not necessarily be maintained (e.g., may be varied). For example, the position changing unit may change the position of the inspection unit 300 during inspection and/or after completing the inspection, such as moving the inspection unit 300 back to its original position before starting another inspection, so that the position of the inspection unit 300 relative to the photographing unit 200 may always be kept constant before starting the inspection. The positions of the photographing unit 200 and the inspection unit 300 relative to the substrate 10 may be fixed when needed, and in this case, the position changing unit may move the photographing unit 200 together with (e.g., concurrently or simultaneously with) the inspection unit 300.

In the apparatus according to the present embodiment, the position of the substrate 10 remains fixed when the substrate 10 rests on the substrate seating portion 100', and instead, the position changing unit changes the position(s) of the photographing unit 200 and/or inspection unit 300 with respect to the substrate seating portion 100' so that inspection is conducted on the semiconductor layer 12 formed on the substrate 10. Thus, the overall size of the apparatus may be considerably reduced because the apparatus does not require a space available to move the substrate 10, requiring a wide area, during the inspection. The position changing unit changes the position(s) of the photographing unit 200 and/or the inspection unit 300 after receiving the change data output from the control unit 400.

When the semiconductor layer 10 has a plurality of crystallized regions separated from each other at intervals (e.g., at predetermined intervals), even in the absence of the markers M1 and M2, the control unit 400 may use brightness data acquired by the photographing unit 200 to identify a position of one of the plurality of crystallized separate regions so that the inspection unit 300 obtains inspection data regarding the corresponding crystallized region. Thereafter, the position changing unit may move the inspection unit 300 by a corresponding interval (e.g., the predetermined interval) so that the inspection unit 300 acquires inspection data regarding the remaining ones of the plurality of crystallized separate regions.

While it is described above that the photographing unit 200 is located (e.g., disposed) above the stage 100 or the substrate seating portion 100' so as to observe a top surface of the substrate 10 which rests on the stage 100 or the substrate seating portion 100', the present invention is not limited thereto. For example, in an apparatus for inspecting crystallization on the substrate 10 having the semiconductor layer 12 formed thereon including the plurality of crystallized separate regions 12b, as shown in FIG. 7, the photographing unit 200 may be located below the stage 100 (e.g., opposite [−z direction] to a direction [+z direction] in which the substrate 10 is loaded onto the stage 100).

Figure 9:
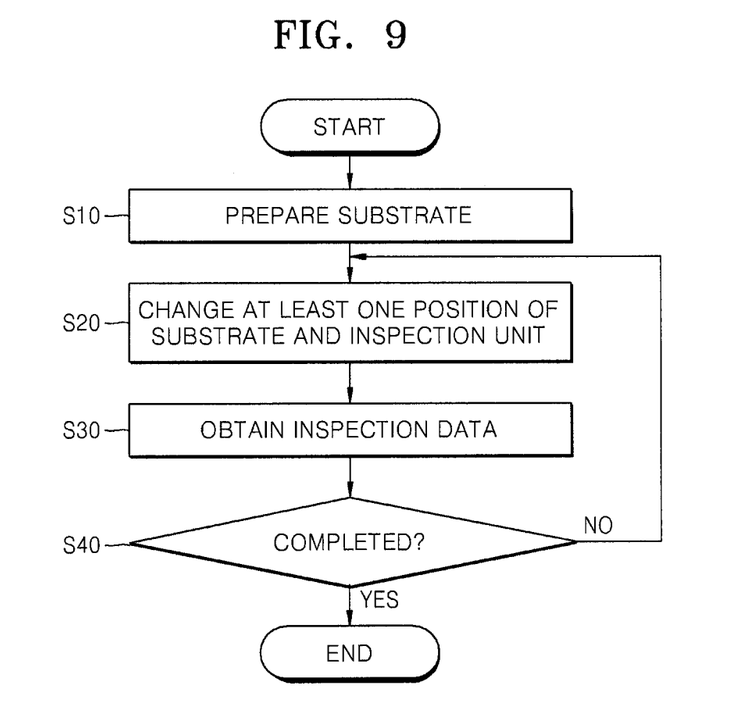
FIG. 9 is a flowchart of a method of inspecting crystallization, according to an embodiment of the present invention.

FIG. 9 is a flowchart of a method of inspecting crystallization, according to an embodiment of the present invention.

Referring to FIG. 9, in the method of inspecting crystallization according to the present embodiment, a substrate having a semiconductor layer formed thereon with a plurality of crystallized separate regions is prepared (S10). Then, at least one position of the substrate and an inspection unit is changed based on image data acquired regarding the semiconductor layer on the substrate so as to obtain inspection data regarding at least one of (e.g., some of) the plurality of crystallized separate regions in the semiconductor layer (S20).

Subsequently, the inspection data regarding the at least one of (e.g., some of) the plurality of crystallized separate regions is obtained (S30). It is then determined whether inspection is completed (S40), and if the inspection is completed, the method stops. Conversely, if the inspection is not completed and so as to obtain inspection data regarding other crystallized separate regions, the method proceeds (or returns) to operation S20 to change the at least one position of the substrate and the inspection unit based on the image data acquired regarding the semiconductor layer on the substrate. Then, inspection data regarding other ones of the plurality of crystallized separate regions in the semiconductor layer is obtained (S30). By repeatedly performing operations S20 and S30 in this way, the entire inspection of crystallization is conducted.

In operation S20, changing at least one position of the substrate and the inspection unit based on the image data acquired regarding the semiconductor layer on the substrate, the position of the substrate or the inspection unit may be changed by using or according to brightness data in the acquired image data.

More specifically, as described above with reference to FIG. 5, in operation S20, the position of the substrate or the inspection unit may be changed by determining that the portion A2 of the semiconductor layer having a brightness in a second brightness range and being between the remaining portions A1 having a brightness in a first brightness range is one of the plurality of crystallized separate regions, wherein the second brightness range is greater than the first brightness range. Alternatively, in operation S20, the position of the substrate or the inspection unit may be changed by determining that in the portions A1 and A2 of the semiconductor layer located between other portions of the semiconductor layer having the peak brightnesses P1 and P2, the portion A2 having a brightness within a brightness range (e.g., a predetermined brightness range) greater than a brightness Bp (e.g., a set brightness Bp) is one of the plurality of crystallized separate regions (e.g., the control unit can determine that one of the plurality of crystallized separate regions is a portion of the semiconductor layer having a brightness between peak brightnesses and in a preset brightness range).

The method of inspecting crystallization according to the present embodiment may prevent the occurrence of noise due to inspection of an uncrystallized region as well as allow inspection of the plurality of crystallized separate regions, even when the semiconductor layer has the plurality of separate regions crystallized instead of the entire region. The method may also allow automatic inspection of crystallization on the plurality of crystallized separate regions.

Figure 10:
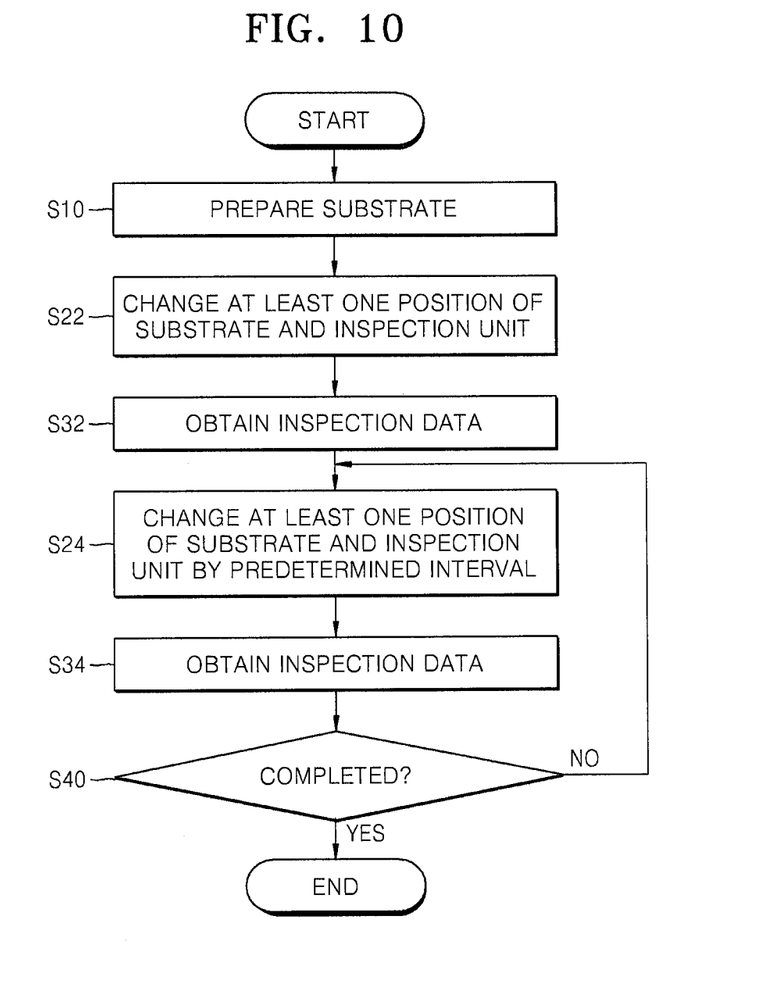
FIG. 10 is a flowchart of a method of inspecting crystallization, according to another embodiment of the present invention.

FIG. 10 is a flowchart of a method of inspecting crystallization, according to another embodiment of the present invention.

Referring to FIG. 10, in the method of inspecting crystallization according to the present embodiment, a substrate having a semiconductor layer formed thereon including a plurality of crystallized regions separated from each other at intervals (e.g., at predetermined intervals) is prepared (S10). Then, at least one position of the substrate and an inspection unit is changed based on image data acquired regarding markers on the substrate so as to obtain inspection data regarding at least one of the plurality of crystallized separate regions in the semiconductor layer (S22), as described above with reference to FIG. 8.

Subsequently, the inspection data regarding at least one of the plurality of crystallized separate regions in the semiconductor layer is obtained (S32). The at least one position of the substrate and the inspection unit is then changed by the interval (e.g., the predetermined interval) so as to obtain inspection data regarding another one of the plurality of crystallized separate regions (S24), and inspection data regarding the another one of the plurality of crystallized separate regions is obtained (S34).

Thereafter, it is determined whether inspection is completed (S40), and if the inspection is completed, the method stops. Conversely, if the inspection is not completed and to obtain inspection data regarding other ones of the plurality of crystallized separate regions, the method proceeds (or returns) to operation S24 so as to change the at least one position of the substrate and the inspection unit by the interval (e.g., predetermined interval). Then, inspection data regarding the other ones of the plurality of crystallized separate regions in the semiconductor layer is obtained (S34). By repeatedly performing operations S24 and S34 in this way, the entire inspection of crystallization is conducted.

The method of inspecting crystallization according to the present embodiment may prevent the occurrence of noise due to inspection of an uncrystallized region as well as allow inspection of the plurality of crystallized separate regions, even when a semiconductor layer has the plurality of separate crystallized regions instead of the entire region of the semiconductor layer being crystallized. The method according to the present embodiment may also allow automatic inspection of crystallization of the plurality of crystallized separate regions.

While the present invention has been particularly shown and described with reference to example embodiments thereof, it will be understood by those of ordinary skill in the art that various changes in form and details may be made therein without departing from the spirit and scope of the present invention as defined by the following claims and their equivalents.

What is claimed is:

1. An apparatus for inspecting crystallization, the apparatus comprising:
   a stage configured to change a position of a substrate, the substrate being seated thereon and comprising a semiconductor layer, the semiconductor layer comprising a plurality of crystallized regions separated from each other;
   a camera configured to acquire image data regarding the semiconductor layer;
   a visual inspection unit configured to obtain inspection data regarding at least one of the plurality of crystallized regions of the semiconductor layer; and
   a controller configured to output change data regarding a change in the position of the substrate according to the brightness data in the image data acquired by the camera, such that the visual inspection unit can obtain the inspection data regarding the at least one of the plurality of crystallized separate regions,
   wherein the controller is further configured to determine that one of the plurality of crystallized separate regions is a portion of the semiconductor layer having a brightness in a second brightness range and located between other portions of the semiconductor layer having brightnesses in a first brightness range, and
   wherein the second brightness range comprises values that are greater than those of the first brightness range.

2. An apparatus of for inspecting crystallization, the apparatus comprising:

a stage configured to change a position of a substrate, the substrate being seated thereon and comprising a semiconductor layer, the semiconductor layer comprising a plurality of crystallized regions separated from each other;

a camera configured to acquire image data regarding the semiconductor layer;

a visual inspection unit configured to obtain inspection data regarding at least one of the plurality of crystallized regions of the semiconductor layer; and a controller configured to output change data regarding a change in the position of the substrate according to brightness data in the image data acquired by the camera, such that the visual inspection unit can obtain the inspection date regarding the at least one of the plurality of crystallized separate regions, wherein the controller is further configured to determine that one of the plurality of crystallized separate regions is a portion of the semiconductor layer having a brightness between peak brightnesses and in a present brightness range.

3. The apparatus of claim 1, wherein a position of the camera is fixed relative to a position of the visual inspection unit.

4. An apparatus for inspecting crystallization, the apparatus comprising:

a substrate seating portion on which a substrate is seated, the substrate comprising a semiconductor layer, the semiconductor layer comprising a plurality of crystallized regions separated from each other;

a camera configured to acquire image data regarding the semiconductor layer;

a visual inspection unit configured to acquire inspection data regarding at least one of the plurality of crystallized regions of the semiconductor layer, the camera and the visual inspection unit each being configured to change position with respect to the substrate seating portion; and a controller configured to output change data regarding a change in the positions of the camera and the visual inspection unit according to brightness data in the image data acquired by the camera, such that the visual inspection unit can obtain inspection data regarding the at least one of the plurality of crystallized separate regions, wherein the controller is further configured to determine that one of the plurality of crystallized separate regions is a portion of the semiconductor layer having a brightness in a second brightness range and located between other portions of the semiconductor layer having brightnesses in a first brightness range, and wherein the second brightness range comprises values that are greater than those of the first brightness range.

5. An apparatus of for inspecting crystallization, the apparatus comprising:

a substrate seating portion on which a substrate is seated, the substrate comprising a semiconductor layer, the semiconductor layer comprising a plurality of crystallized regions separated from each other;

a camera configured to acquire image data regarding the semiconductor layer;

a visual inspection unit configured to acquire inspection data regarding at least one of the plurality of crystallized regions of the semiconductor layer, the camera and the visual inspection unit each being configured to change position with respect to the substrate seating portions; and a controller configured to output change data regarding a change in the position of the camera and the visual inspection unit according to brightness data in the image data acquired by the camera, such that the visual inspection unit can obtain inspection data regarding the at least one of the plurality of crystallized separate regions, wherein the controller is further configured to determine that one of the plurality of crystallized separate regions is a portion of the semiconductor layer having a brightness between peak brightnesses and in a present brightness range.

6. The apparatus of claim 4, wherein a position of the camera is fixed relative to a position of the visual inspection unit.

7. A method of fabricating a display, the method comprising:

preparing a substrate comprising a semiconductor layer comprising a plurality of crystallized regions separated from each other;

changing at least one position of the substrate or a visual inspection unit according to image data acquired regarding the semiconductor layer to obtain inspection data regarding at least one of the plurality of crystallized separate regions;

obtaining the inspection data regarding the at least one of the plurality of crystallized separate regions;

changing the at least one position of the substrate or the visual inspection unit according to the image data acquired regarding the semiconductor layer to obtain inspection data regarding another one of the plurality of crystallized separate regions; and obtaining the inspection data regarding the another one of the plurality of crystallized separate regions, wherein the at least one position of the substrate or the visual inspection unit is changed according to brightness data in the acquired image data, wherein the at least one position of the substrate or the visual inspection unit is changed by determining that one of the plurality of crystallized separate regions is a portion of the semiconductor layer having a brightness in a second brightness range and located between other portions of the semiconductor layer having brightnesses in a first brightness range, and wherein the second brightness range comprises values that are greater than those of the first brightness range.

8. A method of fabricating a display, the method comprising:

preparing a substrate comprising a semiconductor layer comprising a plurality of crystallized regions separated from each other;

changing at least one position of the substrate or a visual inspection unit according to image data acquired regarding the semiconductor layer to obtain inspection data regarding at least one of the plurality of crystallized separate regions;

obtaining the inspection data regarding the at least one of the plurality of crystallized separate region;

changing the at least one position of the substrate or the visual inspection unit according to the image data acquired regarding the semiconductor layer to obtain inspection data regarding another one of the plurality of crystallized separate regions; and obtaining the inspection data regarding the another one of the plurality of crystallized separate regions, wherein the at least one position of the substrate or the visual inspection unit is changed according to the brightness data in the acquired image data, and wherein the at least one position of the substrate or the visual inspection unit is changed by determining that one of the plurality of crystallized separate regions is a portion of the semiconductor layer having a brightness between peak brightnesses and in a brightness range.

9. The method of claim 7, wherein the changing of the at least one position of the substrate or the visual inspection unit to obtain inspection data regarding the another one of the plurality of crystallized separate regions and the obtaining of the inspection data regarding the another one of the plurality of crystallized separate regions are repeated.

* * * * *